United States Patent [19]

Agrawal et al.

[11] Patent Number: 5,149,798
[45] Date of Patent: Sep. 22, 1992

[54] PROCESS FOR SYNTHESIZING OLIGONUCLEOTIDES AND THEIR ANALOGS ADAPTABLE TO LARGE SCALE SYNTHESES

[75] Inventors: Sudhir Agrawal; Paul C. Zamecnik, both of Shrewsbury, Mass.

[73] Assignee: Worcester Foundation for Experimental Biology, Shrewsbury, Mass.

[21] Appl. No.: 334,679

[22] Filed: Apr. 6, 1989

[51] Int. Cl.$^5$ .............................. C07H 21/00
[52] U.S. Cl. ...................... 536/27; 536/28; 536/29
[58] Field of Search ............... 536/27, 28, 29

[56] References Cited

U.S. PATENT DOCUMENTS 4,959,463  9/1990  Froehler et al. .................. 536/27

OTHER PUBLICATIONS

B. L. Gaffney and R. A. Jones, Tet. Let. 29: 2619-2622 (1988).
P. J. Garegg, et al., Tet. Let. 27: 4051-4054, 4055-4058 (1986).
B. C. Froehler et al., Nucl. Acid Res.,14: 5399-5407 (1986).
B. C. Froehler, Tet. Let. 27: 5575-5578 (1986).
B. C. Froehler and M. D. Matteucci, Tet. Let. 27: 469-472 (1986).
Garegg et al (II), Chemical Scripta, vol. 26, pp. 59-62, 1985.
Garegg et al (III), Chemica Scripta, vol. 25, pp. 280-282, 1985.
Nemer et al (I)., Tetrahedron Letters, vol. 21, pp. 4149-4152, 4153-4154 (1980).

Primary Examiner—Johnnie R. Brown
Assistant Examiner—L. Eric Crane
Attorney, Agent, or Firm—Allegretti & Witcoff, Ltd.

[57] ABSTRACT

A process of producing synthetic oligonucleotides on a small or large scale using H-phosphonate nucleoside monomers is described. The process can be used to synthesize oligonucleotides of any length, including oligodeoxyribonucleotides and oligoribonucleotides. The process results in a coupling efficiency of greater than 97% and consumes only two to three equivalents of monomer to activator per coupling reaction. In addition, the process does not require a separate capping step and capping reagent because the activating reagent serves a self-capping function thereby preventing elongation of failed sequences. The H-phosphonate linkages of the fully synthesized oligonucleotide can be oxidized with a variety of reagents to obtain either phosphate diester or other types of modified oligonucleotides.

2 Claims, 8 Drawing Sheets

MODEL 8600/8700-FLOW MAP

FIG.4

| STEP | LENGTH | FUNCTION | OUTPUTS |
|------|--------|----------|---------|
| 1 | 05.0 | AUX 1 | = 5, 15, 16, 17, 18 |
| 2 | 02.0 | WAIT | |
| 3 | 05.0 | AUX 1 | = 5, 15, 16, 17, 18 |
| 4 | | REPEAT | STEP 02  5X |
| 5 | 00.3 | COUPLE | 14, 15, 16, 17, 18 |
| 6 | 00.3 | AUX 1 | = 8, 14, 15, 16, 17, 18 |
| 7 | | REPEAT | STEP 05  12X |
| 8 | 10.0 | WAIT | |
| 9 | 00.3 | COUPLE | 14, 15, 16, 17, 18 |
| 10 | 00.3 | AUX 1 | = 8, 14, 15, 16, 17, 18 |
| 11 | | REPEAT | STEP 09  12X |
| 12 | 10.0 | WAIT | |
| 13 | 00.3 | COUPLE | 14, 15, 16, 17, 18 |
| 14 | 00.3 | AUX 1 | = 8, 14, 15, 16, 17, 18 |
| 15 | | REPEAT | STEP 13  12X |
| 16 | 10.0 | WAIT | |
| 17 | 05.0 | WASH B | 7, 14, 15, 16, 17, 18 |
| 18 | | REPEAT | STEP 16  10X |
| 19 | 20.0 | WASH B | 7, 14, 15, 16, 17, 18 |
| 20 | 05.0 | FLUSH B | 7, 14, 19 |
| 21 | 10.0 | FLUSH A | 1, 19 |
| 22 | | SUB | 0  RETURN |

FIG.5

| STEP | LENGTH | FUNCTION | OUTPUTS |
|---|---|---|---|
| 1 | 05.0 | AUX 1 | * 5, 15, 16, 17, 18 |
| 2 | 02.0 | WAIT | |
| 3 | 04.0 | AUX 1 | * 5, 15, 16, 17, 18 |
| 4 | | REPEAT | STEP 02  5X |
| 5 | 00.3 | COUPLE | 14, 15, 16, 17, 18 |
| 6 | 00.3 | AUX 1 | * 8, 14, 15, 16, 17, 18 |
| 7 | | REPEAT | STEP 05  12X |
| 8 | 10.0 | WAIT | |
| 9 | 00.3 | COUPLE | 14, 15, 16, 17, 18 |
| 10 | 00.3 | AUX 1 | * 8, 14, 15, 16, 17, 18 |
| 11 | | REPEAT | STEP 09  12X |
| 12 | 10.0 | WAIT | |
| 13 | 00.3 | COUPLE | 14, 15, 16, 17, 18 |
| 14 | 00.3 | AUX 1 | * 8, 14, 15, 16, 17, 18 |
| 15 | | REPEAT | STEP 13  12X |
| 16 | 10.0 | WAIT | |
| 17 | 00.3 | COUPLE | 14, 15, 16, 17, 18 |
| 18 | 00.3 | AUX 1 | |
| 19 | | REPEAT | STEP 17  20X |
| 20 | 10.0 | WAIT | |
| 21 | 05.0 | WASH B | 7, 14, 15, 16, 17, 18 |
| 22 | 02.0 | WAIT | |
| 23 | | REPEAT | STEP 21  5X |
| 24 | 10.0 | WASH B | 7, 14, 15, 16, 17, 18 |
| 25 | 02.0 | FLUSH A | 1, 19 |
| 26 | 02.0 | FLUSH B | 7, 14, 19 |
| 27 | | SUB 0 | RETURN |

FIG.6

| STEP | LENGTH | FUNCTION | OUTPUTS |
|---|---|---|---|
| 1 | 01.0 | FLUSH B | 7, 14, 19 |
| 2 | 02.0 | FLUSH A | 1, 19 |
| 3 | 05.0 | WASH A | 1, 15, 16, 17, 18 |
| 4 | 02.0 | WAIT | |
| 5 | | REPEAT STEP 03 5X | |
| 6 | 01.0 | DEBLOCK * | 2, 19, 20, 22, 24, 26 |
| 7 | 30.0 | DEBLOCK | 2, 15, 16, 17, 18, 20, 22, 24, 26 |
| 8 | 10.0 | WAIT | |
| 9 | 30.0 | DEBLOCK | 2, 15, 16, 17, 18, 20, 22, 24, 26 |
| 10 | 10.0 | WAIT | |
| 11 | 20.0 | DEBLOCK | 2, 15, 16, 17, 18, 20, 22, 24, 26 |
| 12 | 10.0 | WAIT | |
| 13 | 10.0 | WASH A * | 1, 15, 16, 17, 18, 20, 22, 24, 26 |
| 14 | 01.0 | AUX 3 * | 1, 2, 3, 4 |
| 15 | 20.0 | WASH A | 1, 15, 16, 17, 18 |
| 16 | 05.0 | FLUSH B | 7, 14, 19 |
| 17 | 10.0 | WASH B | 7, 14, 15, 16, 17, 18 |
| 18 | | SUB CPL | |
| 19 | | GO WH BA 03 | |
| 20 | 15.0 | WASH A | 1, 15, 16, 17, 18 |
| 21 | 10.0 | WAIT | |
| 22 | 15.0 | WASH A | 1, 15, 16, 17, 18 |
| 23 | 10.0 | WAIT | |

FIG.8
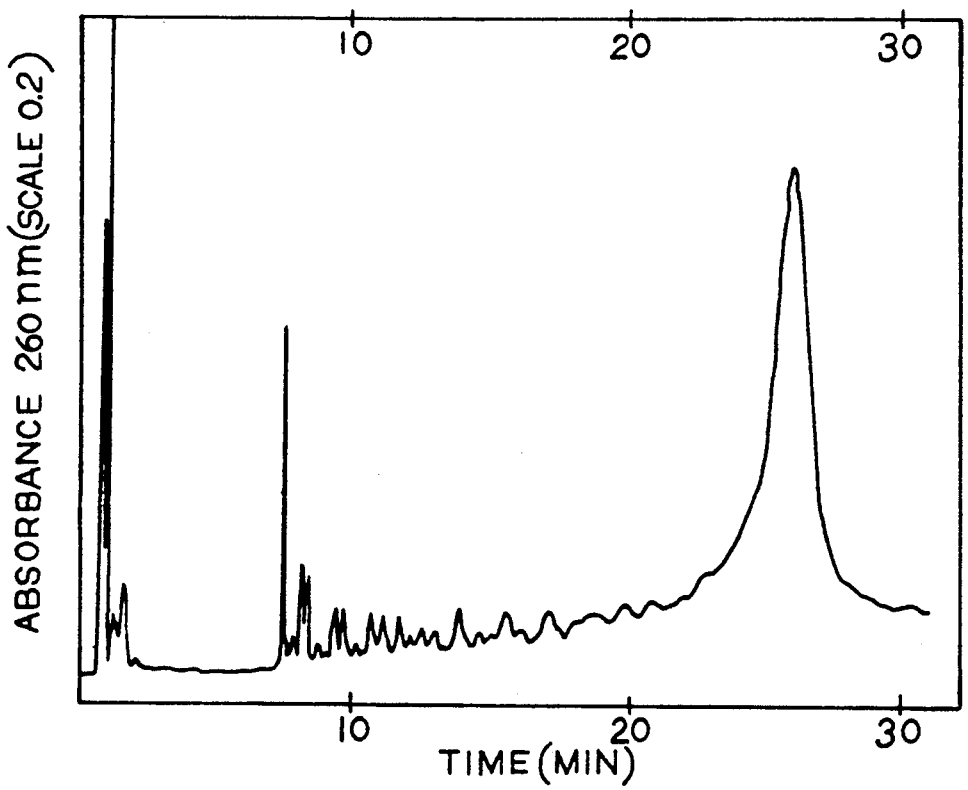
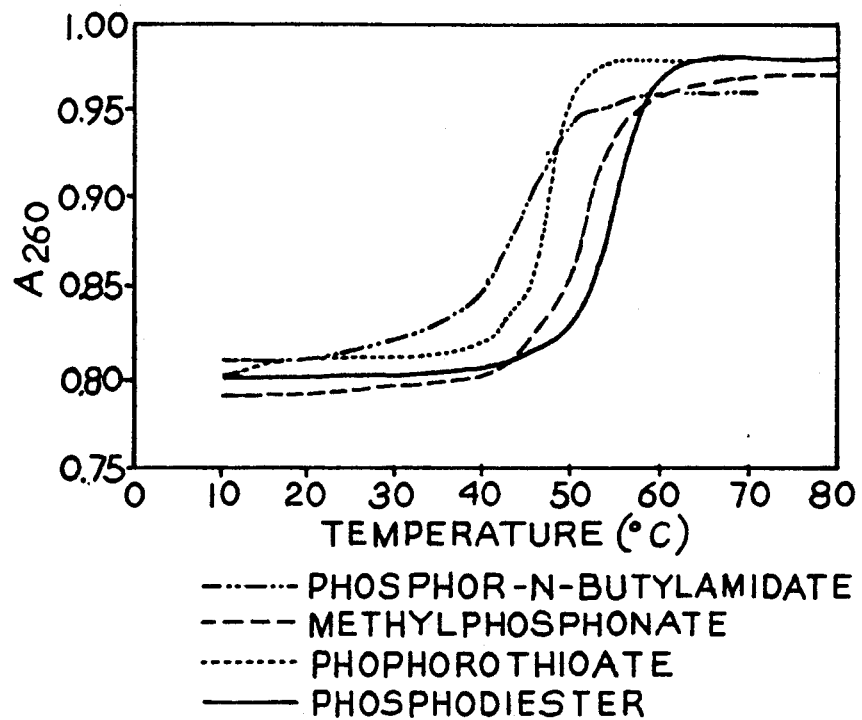
FIG.9
—·—·— PHOSPHOR-N-BUTYLAMIDATE
— — — METHYLPHOSPHONATE
·········· PHOPHOROTHIOATE
——— PHOSPHODIESTER

PROCESS FOR SYNTHESIZING OLIGONUCLEOTIDES AND THEIR ANALOGS ADAPTABLE TO LARGE SCALE SYNTHESES

FUNDING

Work described herein was supported by funding from the National Institutes of Health.

BACKGROUND OF THE INVENTION

Simple methods for synthesizing and purifying oligonucleotides are now in great demand due to the utility of synthetic oligonucleotides in a wide variety of molecular biological techniques. Until recently, the method of choice for synthesizing oligonucleotides was the beta-cyanoethyl phosphoramidite method. S. L. Beaucage and M. H. Caruthers, Tet. Let. 22: 1859 (1981). In the phosphoramidite procedure, the first nucleotide (monomer 1) is bound by its 3' hydroxyl to a solid matrix while its 5' hydroxyl remains available for binding. The synthesis of the first internucleotide link is carried out by mixing bound monomer 1 with a second nucleotide that has a reactive 3'diisopropyl phosphoramidite group on its 3' hydroxyl and a blocking group on its 5' hydroxyl (monomer 2). In the presence of a weak acid, coupling of monomer 1 and monomer 2 occurs as a phosphodiester with phosphorus in a trivalent state. This is oxidized giving a phosphotriester where the phosphorus is pentavalent. The protecting group is then removed from monomer 2 and the presence is repeated.

Oligonucleotide synthesis using nucleoside H-phosphonates has been reported (Hale et al., *J. Chem. Soc.*, p. 3291 (1957); Sekine et al., *Tet. Let.*, 20:1145 (1979); Garegg et al., *Chemica Scripta*, 26:59 (1986) but became practical only with the recent introduction of pivaloyl chloride (trimethyl acetyl chloride) as the condensing agent. There since have been reported of successful use of this method in both deoxyribonucleotide and ribonucleotide syntheses. Garegg et al., *Tet. Let.*, 27:4051-4054 (1986); Froehler et al., *Nucl. Acid. Res.*, 14:5399-5407 (1986) ; Garegg et al., *Tet. Let.*, 27:4055-4058 (1986). The H-phosphonate method offers several advantages over the beat-cyanoetyl phosphoramidite method. The H-phosphonate method can be accomplished in a shorter cycle time and the 3' phosphonate monomers have greater stability than that of the corresponding 3'-phosphoramidiates. Finally, a simple reaction can be used to prepare backbone-modified DNA or RNA from the H-phosphonate synthesis product.

The H-phosphonate methods of Froehler et al. and Garegg et al., although adequate for small scale synthesis (i.e., less than 1 μmole), are not practical on a large scale (e.g., 10-20 μmole). The main reason it is not practical is that the methods reported by these groups require 20-30 equivalents of monomer per coupling reaction. At this rate, the monomer consumption costs represent approximately 60% of the oligonucleotide assembly cost.

In a recent publication, Gaffney et al. report an effort to scale up H-phosphonate oligonucleotide synthesis to the 10-20 μmole range, while reducing the monomer equivalents consumed per coupling reaction. Gaffney et al., *Tet. Let.*, 29:2619-2622 (1988). However, in synthesizing an 8-mer (consuming 1.53 equivalents of H-phosphonate) and a 26-mer (consuming 5.5 equivalents of H-phosphonate), Gaffney'group reported an average coupling yield of only 81% and 87%, respectively. Because of these relatively low coupling efficiency as compared with prior art methods, the authors found it necessary to employ a separate capping step using cyanoethyl H-phosphonate to prevent the elongation of truncated failed sequences in subsequent synthetic cycles. This extra step was necessary because the self-capping efficiency for pivaloyl chloride (the coupling reagent) was found to be too low. According to the method of Gaffney et al., which assumed a 94% coupling yield, the expected result of a 20-mer synthetic reaction would be a crude mixture consisting of 24% product (20-mer) and 76% short chains (e.g., 19-mers, 18-mers, etc.).

In sum, the presently available methods for oligonucleotide synthesis which have ben shown to produce relatively efficient coupling yields (i.e., greater than 97%) have not proven to be cost-effective in large scale reactions because these methods require the use of 20-30 equivalents of monomer per coupling reaction. In addition, the presently available methods which are more cost-effective in large scale reactions have proven unsatisfactory due to less efficient coupling yields.

A method of oligonucleotide synthesis which produces relatively efficient coupling yields and is cost-effective for large scale reactions would be very useful.

SUMMARY OF THE INVENTION

The present invention relates to a method of synthesizing oligonucleotides on a small or a large scale using H-phosphonate nucleoside monomers. More particularly, the method results in a coupling efficiency of more than 97% and consumes approximately 2-2.5 equivalents excess of monomer to support bound 5' oligonucleoside or 5'-hydroxyl of a growing chain per coupling reaction. In addition, the method does not require a separate capping step beacuse the activating reagent serves a self-capping function which prevents elongation of failed sequences. Because the method of the present invention greatly reduces monomer consumption, the monomer cost is reduced by 10-fold and makes large scale synthesis much more cost-effective than presently available methods.

In one aspect, the present method consists of attaching to a solid support one end (e.g., the 3'-end) of nucleoside H-phosphonate monomers in which the group present at the other end (e.g., 5'-end hydroxyl) is protected with an acid labile group or a base labile group. The protecting group (here, a 5'-protected nucleoside H-phosphonate) is then coupled to the support-bound growing chain tin the presence of activator. This procedure is repeated as needed, with each step or cycle resulting in addition of an H-phosphonate nucleoside monomer to the support-bound nucleosides, which form a growing nucleoside chain. The activator R-C(O)-Cl (where R is a alkyl, aryl, heteroaryl, etc.) itself is a reactive moiety and can react with the hydroxyl of the growing chain, thereby stopping chain growth. However, the activator can also react with nucleoside H-phosphonate monomer to form an activated mixed anhydride which is more reactive with the 5'-hydroxyl of the growing nucleoside chain than is the activator itself.

The procedure is repeated to add successive nucleoside H-phosphonate monomers in a step-wise manner until the appropriate oligonucleotide is obtained. The H-phosphonate linkages of the fully synthesized oligonucleotide can then be oxidized with a variety of reagents to obtain either phosphate diester or other type of modified nucleotides. The resulting oligonucleotide is then removed from the support using known techniques.

The above and other features of the invention including various novel details of construction and combinations of parts will now be more particularly described with reference to the accompanying drawings and pointed out in the claims. It will be understood that the particular method of oligonucleotide synthesis embodying the invention is shown by way of illustration only and not as a limitation of the invention. The principles and features of this invention may be employed in varied and numerous embodiments without departing from the scope of the invention.

BRIEF DESCRIPTION OF THE DRAWINGS

FIG. 4 is a preferred program developed for synthesizing an oligodeoxyribonucleotide using one column on the Biosearch 86009/8700 Automated DNA Synthesizer.

FIG. 5 is a preferred program developed for synthesizing an oligoribonucleotide using one column on the Biosearch 8600/8700 Automated DNA Synthesizer.

FIG. 6 is a preferred program developed for deprotecting the 5' end group of the growing oligonucleotide chain.

FIG. 8 depicts HPLC data analysis of the product mixture of a 20-mer phosphorothioate analog of oligodeoxynucleotide using a partisphere SAX, 4 mm × 12.5 cm column. The gradient used was 100% 1 mM $KH_2PO_4$ (pH 6.3), 0–100% 400 mM $KH_2PO_4$ (pH 6.3)/60% formamide in 30 minutes.

FIG. 9 is a melting curve of an oligonucleotide with four different phosphate backbones hybridizing to their complementary phosphodiester sequences.

DETAILED DESCRIPTION OF THE INVENTION

Figure 1:
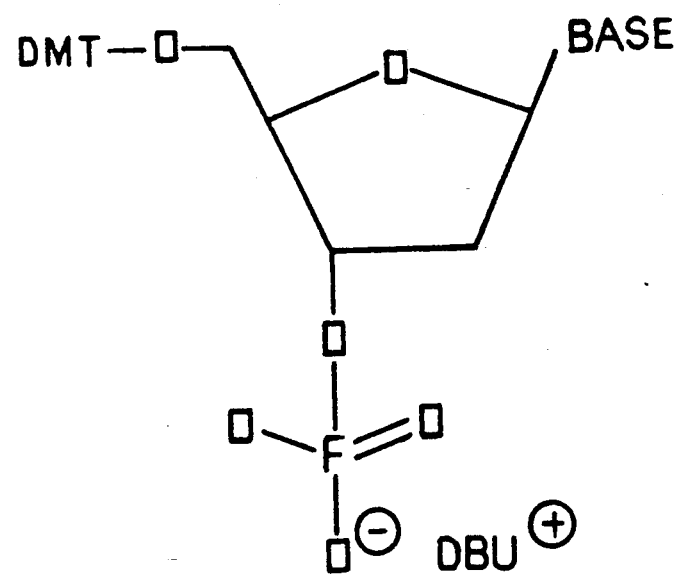
FIG. 1 is a schematic representation of an H-phosphonate monomer.

The present invention relates to an improved method for producing oligonucleotides using H-phosphonate nucleoside monomers. In particular, the method makes it possible for monomer coupling to be carried out efficiently (e.g., greater than 97%) with consumption of smaller amounts (e.g., 2–3 equivalents) of monomer per coupling reaction than used in presently available methods. Furthermore, failed sequences are capped by excess activation reagent in the coupling step, thereby obviating the need for a separate capping step and reagent. The oligonucleotides produced in the present method can be ribonucleotides as well as deoxyribonuceotides, homosequences as well as heterosequences and of any selected length (e.g., from 15-mers to 60-mers).

In nature, the polymerization of ribonucleotides and deoxyribonucleotides is directed by a template strand. An RNA or DNA polymerize molecule binds to the template strand and adds nucleotides, complementary to the nucleotides found in the template strand, to the nascent nucleotide chain. The order of the nucleotides in the newly synthesized strand is therefore determined by the order of the nucleotides in the template strand.

In vitro methods of oligonucleotide synthesis do not employ a template strand to control the order of monomer addition. Reactive groups are simply brought into proximity and a 5'-3' bond is formed. The first nucleotide (monomer 1) is generally bound to a solid support medium by one end (e.g., the 3' hydroxyl group) with the result that only its other end (e.g., its 5' hydroxyl end) is able to react. The next (incoming) nucleotide (monomer 2) is blocked or protected by a chemical group (e.g., 4'4' dimethyoxytrityl (DMT), only at one end (e.g., the 5' hydroxyl). The other end (e.g., the 3' hydroxyl) is then able to react with the first end (e.g., the 5' hetodroxyl) of bound monomer 1. If monomer 2 were active at both the 3' and the 5' ends, multiple additions could occur on a single oligonucleotide chain in a single synthetic cycle. Therefore, for example, instead of one adenine monomer being added to the nascent oligonucleotide chain in a certain position, two or three adenines would be added at that position.

Following bond formation between, for example, the 3' end of monomer 2 and the 5' end of monomer 1, unreacted monomers are washed from the reaction vessel. In the next step, the 5' end of the bound oligonucleotide chain is deprotected by removing the protecting group, using an appropriate deprotecting agent. Another addition cycle can then proceed.

The syntheses described herein were carried out using a solid support to which the first nucleotide (monomer 1) is bound by its 3' hydroxyl group, but the method can also be used with a solid support to which the first nucleotide is bound by its 5' end. In addition, the synthesis described herein uses nucleoside H-phosphonate monomers. In other words, the nucleotide monomers are nucleoside H-phosphates. However, more than one nucleoside can be added in a given cycle by using polynucleoside H-phosphonates (e.g., di- or tri-nucleoside phosphonates). Polynucleoside H-phosphonates are prepared by reacting a bound or unbound nucleoside to a second nucleoside phosphonate. The synthesis can be conducted on any automated DNA synthesizer.

When carried out on an automated synthesizer, the reaction vessel can be a column of any volume. Within the reaction vessel is a slid support medium, (e.g. controlled pore glass [CPG], cellulose, polystyrene, etc.) to which nucleoside H-phosphates are bond. The column is fitted with an input port and an output port through which solutions are passed into and out of the reaction vessel. It is important that the reaction vessel and solid support medium be well saturated with an inert solution (e.g. pyridine-acetonitrile [1:1]) prior to introduction of the H-phosphonate monomers and the activator solution, which are also dissolved in the same inert solution. As mentioned earlier, the reaction vessel can be a column of any volume, depending on the scale of the synthesis (the amount of solid support to be used). The volume must be appropriate to contain the particular bed volume of solid support and, in general, 10–15% of the volume of the vessel will be empty space so that the nucleoside H-phosphonate monomer and activator are properly mixed when they are passed through the reaction vessel (column) in pulses during the coupling step.

Protected, 5'-dimethoxytrityl 3' nucleotide H-phosphonates can be obtained as 1,8-diazabicylo (5.4.0) undec-7-ene (DBU) triethylamine (TEA) salts or they can be prepared using known techniques. Froehler et al., *Nucl. Acid. Res.*, 14: 5399–5407 (1986). FIG. 1 shows an H-phosphonate monomer having a DMT protected 5' end and an H-phosphonate group at the 3' end. Prior to the synthesis reaction, each of the four H-phosphonate salts is dissolved in a mixture of an inert solution (e.g., pyridine-acetonitrile).

In one embodiment of the present invention, the ratio of monomer nucleoside H-phosphonate to activator solution is 1:10. However, the ratio of nucleoside H-phosphonate monomer to activator will vary depending on the monomers used and the oligomer to be synthesized. The appropriate ratio will be determined empirically. In one embodiment, the activator used is pivaloyl chloride or adamantane carboxyl chloride in pyridine-acetonitrile.

The mixture of nucleoside H-phosphonate and activator (e.g., pivaloyl chloride or adamantane carboxyl chloride) yields a mixed anhydride of nucleoside which reacts rapidly with the 5'-OH of the growing chain (Garegg, P. J. et al., *Nucleosides and Nucleotides*, 6: 655 (1987)). This mixed anhydride of nucleoside can also react further with pivaloyl chloride to generate a bis-acylphosphite, which can then undergo an Arbusov-type reaction. deVroom, E. et al., *Recl. Trav. Chem. Pays. Bas.*, 106:65 (1987). On a small scale, for example, when only 5–30 mgs (0.2 to 1 μmole, when loading is 30 μmole g$^{-1}$) of support bound nucleoside are employed and the volume of activated nucleoside passing through the column is high (about 30 equivalents excess), reaction times are short enough to avoid this competing reaction. However, this may no longer be true when hundreds of milligrams of CPG are used and the residence time in the column is therefore much longer. Hence, the first concern of using H-phosphonate chemistry for large scale oligonucleotide synthesis is the effect that longer coupling time has on coupling efficiency and the ratio of coupling to capping.

In essence, there are two critical factors for the successful assembly of oligonucleotides on a large scale using H-phosphonate chemistry:

(A) Reactivity of nucleoside H-phosphonate-monomer: Once the nucleoside H-phosphonate is reacted with activator, the product is a mixed anhydride of nucleoside H-phosphonate. The half lie of this activated species is only approximately 15 seconds. Therefore, it should be used up for proper reaction (i.e., to grow oligonucleotide chain) before it forms bis-acylphosphite by reacting with excess activator.

(B) Capping: The ratio of nucleoside H-phosphate monomer to activator is critical. If activator concentration is two low, activation of the nucleoside H-phosphonate monomer will be affected. If the concentration of activator is too high, it will cap the growing chain, and also shift the equilibrium of the reaction to produced more bis-acylphosphite.

For example, if the volume of support employed for large scale synthesis is about 2 ml (e.g., if using 500 mgs CPG, therefore 15 μmole, when loading 30 μmole g$^{-1}$), the coupling step preferably is accomplished so that no activated monomer is residing in the column for more than 10–15 seconds. If the ratio of activator to nucleoside H-phosphonate monomer is greater than required under optimized conditions, the activator will react with the 5'-hydroxyl of the growing chain. In the embodiment of the method of the present invention in which 10 equivalents excess of activator is mixed with 1 equivalent excess of nucleoside H-phosphonate, the caping reaction rate is optimized so that it occurs in less than 1% of the coupling reaction time.

Figure 2:
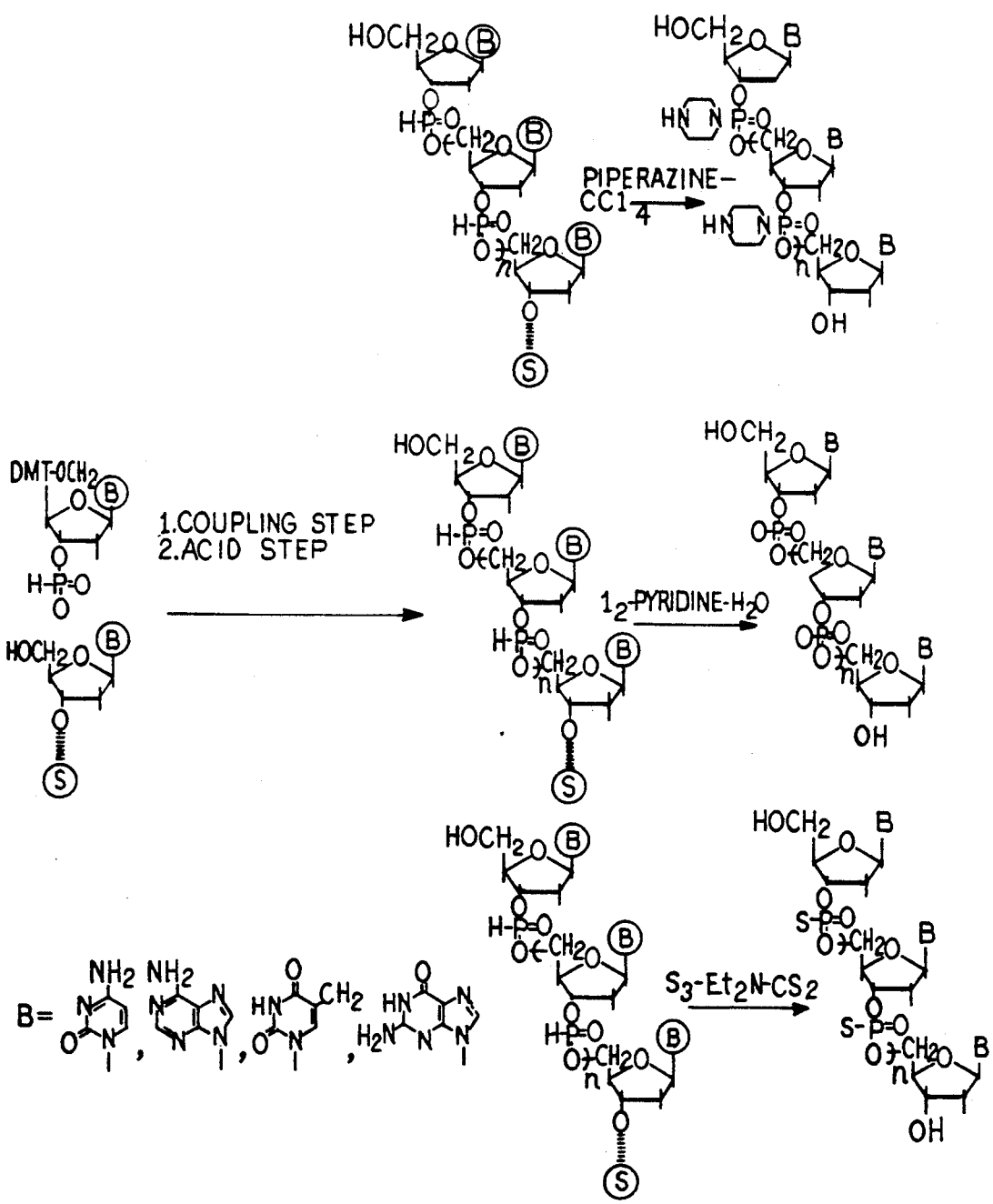
FIG. 2 is a schematic representation of the H-phosphonate synthesis cycle, including some of the different phosphate backbone modifications that can be made to the H-phosphonate intermediate.

FIG. 2 is a schematic representation of the H-phosphonate synthetic cycle and Table 1 sets forth the conditions optimizing oligonucleotide synthesis using one column of the Biosearch 8600/8700 automated DNA synthesizer on a 15 μmole scale synthesis.

TABLE 1

| CYCLE | | | |
|---|---|---|---|
| Step | Reagent | Time | Vol consumed |
| 1. Deprotection | 3% dichloroacetic acid in dichloroethane | 110 sec. (30 sec halt) | 9 ml |
| 2. Wash | acetonitrile | 55 sec. | 8 ml |
| 3. Wash | acetonitrile-pyridine (1:1) | 24 sec. | 3 ml |
| 4. Coupling | 10 mM nucleoside 100 mM activator | 52 sec. | 5–6 ml |
| 5. Wash | acetonitrile | 30 sec. | 4 ml |

In a one column synthesis on a 15 μmole scale, the amount of activated monomer used is only 3 ml (total volume 6 ml, where 3 ml is nucleoside H-phosphonate and 3 ml is activator). The amount used is only 30 μmole for a 15 μmole scale synthesis. The yield per step, as measured by a trityl assay and after deprotection and purification of oligonucleotide, is always greater than 97%. M. Gait, *Oligonucleotide Synthesis: A Practical Approach* p. 90–91, IRL Press Ox for (1984). The same cycle is repeated to add successive H-phosphonate monomers in a step-wise manner until the desired oligonucleotide is obtained.

Figure 3:
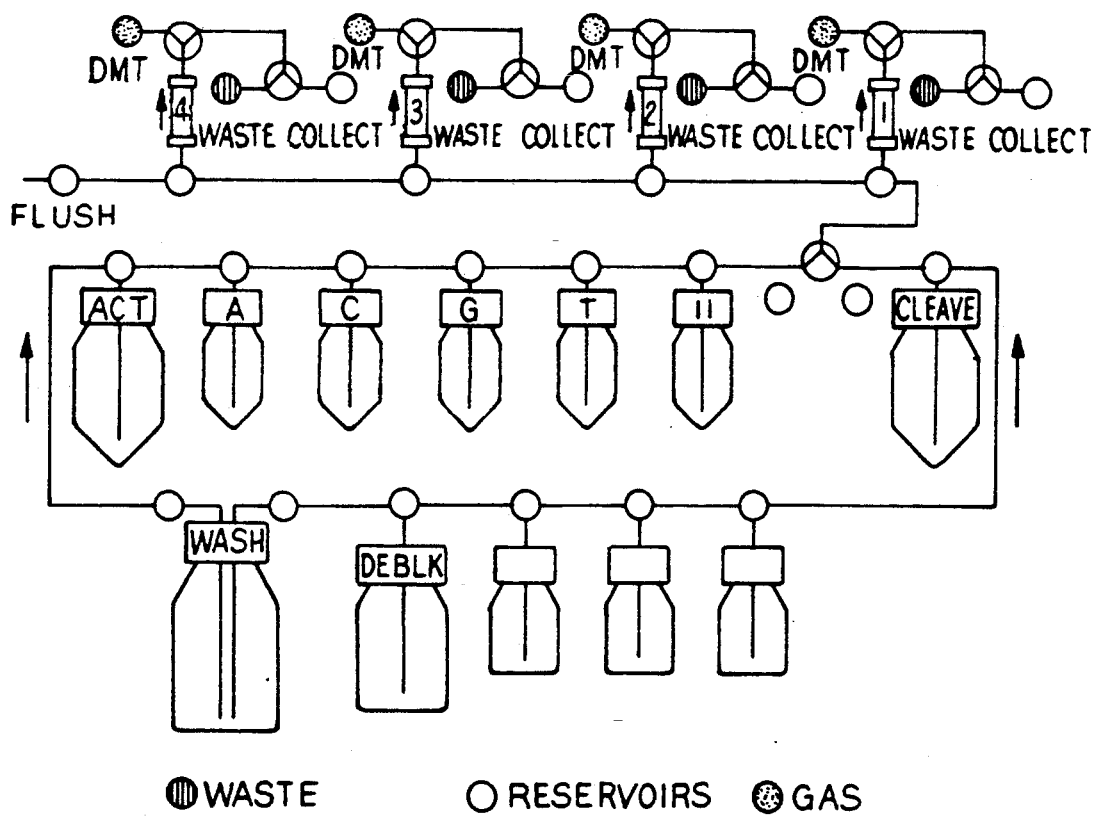
FIG. 3 is a flow map of the Biosearch 8600/8700 Automated DNA Synthesizer.

The above mentioned synthetic cycle is also illustrated in FIG. 4. FIG. 3 is a flow map of the Biosearch 8600/8700 Automated DNA Synthesizer. The output columns in FIGS. 4–6 correspond to the numbers shown on the flow map. Reservoir 3, 4, or 5 contain the inert solution (e.g., pyridine/acetonitrile) wile the other two reservoirs remain empty. Reservoir 8 contains activator and reservoirs 9–12 contain the H-nucleoside monomers.

Using the Biosearch 8600–8700, the activator and monomer nucleoside H-phosphonates are pumped, in pulses of 0.3 second each, for 12 times, thereby filling up the reaction vessel with 2 ml of activated monomer (mixed anhydride) in 3.6 seconds (see Step #7). This is followed by a 10 second halt step (Step #8), during which the activated monomer reacts with support bound nucleoside at its 5'-end. Next, the activator and nucleoside H-phosphonate are pumped 12 times through the columns, in pulses of 0.3 seconds each. Again the reaction vessel is filled with fresh activated monomer (Step #15) and old activated monomer is displaced as waste. There is then another 10 second halt step (Step #16), after which the same steps are repeated. During these steps, only 2 equivalents excess of monomer is being consumed, with the result that the yield per coupling is greater than 97%. The reaction conditions reported here are optimized for the monomers used and the oligonucleotide to be produced changing either the concentration of reagents, the time of coupling or the volume of reagent gives poorer coupling yields.

FIG. 5 illustrates the synthetic cycle for synthesizing an oligoribonucleotide. Because of the slow reactivity of ribonucleoside monomer, the coupling cycle requires 20 more pulses in order to complete the reaction. In a synthesizing the oligonucleotide illustrated in FIG. 5, 3 equivalents of nucleoside monomer was consumed.

FIG. 6 is a preferred program developed for deprotecting the 5' end group of the growing oligonucleotide chain regardless of whether an oligoribonucleotide or an oligodeoxyribonucleotide is being synthesized.

Synthesis using 2, 3 and 4 columns can also be done using the method of the present invention and an automated synthesizer, such as the Biosearch 8600/8700 machine. The coupling program is slightly different in this case. The deprotection and wash steps (steps 1, 2, and 5 in Table 1) are increased by 10% for 2 columns, 20% for 3 columns, and 30% for 4 columns, etc.

As mentioned previously, the reaction vessel can be of any volume, provided that approximately 10-15% of the vessel is empty space. The following is a description of synthesis carried out on a 100 µmole scale (using 2.5 gram support) in a 6 ml reaction vessel. The vessel was designed so that both ends of the column could be attached to the outlet and inlet ports of the Biosearch machine. The time for deprotection of the 5'-end and the following washing steps and coupling cycle were adjusted accordingly.

Table 2 sets forth the conditions for oligonucleotide synthesis using the Biosearch 8600 on a scale of 100 µmoles in a 6 ml reaction vessel.

TABLE 2

| Step | Reagent | Time | Vol. Consumed |
|---|---|---|---|
| 1. Deprotection | 3% DCA in dichloroethane | 3 min. | 30 ml |
| 2. Wash | acetonitrile | 3 min. | 30 ml |
| 3. Wash | acetonitrile-pyridine (1:1) | 1 min. | 12 ml |
| 4. Coupling | 10 mM nucleoside-100 mM activator | 1.44 min. | 30-36 ml |

In this situation, forty 0.3 second pulses of activator and monomer were used, thereby releasing 6 ml of activated monomer. After a halt step of 10 seconds, the cycle was repeated 5 times. The total volume consumed was 30-36 ml (approximately 180 µmole) with the result that only 1.8 equivalent excess monomer was consumed.

Bound oligonucleotide chain having H-phosphonate diester bonds can then be oxidized, using, for example, aqueous iodine, to yield a product having the 3'-5' phosphate diester bonds found naturally in nucleic acids.

Alternatively, the 5'-3' H-phosphonate diester intermediate can be reacted with other reagents to obtain different phosphate backbone-modified oligo-nucleotides. Agrawal, S. et al., *Proc. Natl. Acad. Science USA* 85: 7079-7083 (1988). FIG. 2 illustrates some of the modifying agents that can be reacted with the 5'-3' H-phosphonate diester intermediates and the resultant phosphate-derived analogs.

The bound oligonucleotide chain resulting from the present method is released from the solid support using known methods, such as by treatment with ammonium hydroxide. The product is also recovered by known methods (e.g., reverse phase HPLC, polyacrylamide gel electrophoresis, etc.). It is also possible to use the method described in co-pending U.S. patent application Ser. No. 07/311,111, entitled "Method of Separating Oligonucleotides From a Mixture" by Sudhir Agrawal and Paul Zamecnik, filed Feb. 15, 1989, the teachings of which are incorporated herein by reference.

Figure 7:
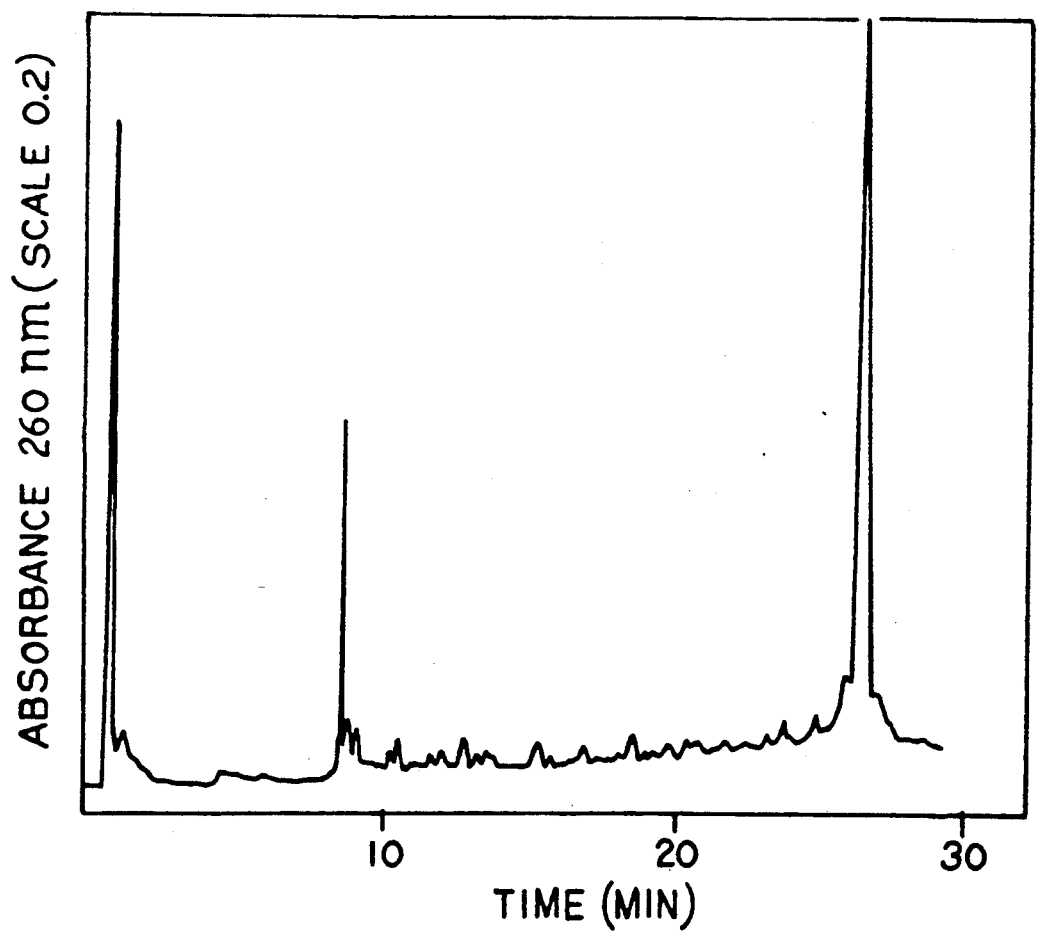
FIG. 7 depicts HPLC data analysis of the product mixture of a 20-mer phosphodiester oligodeoxynucleotide using a partisphere SAX, 4 mm × 12.5 cm column. The gradient used was 100% 1 mM $KH_2PO_4$ (pH 6.3) for 2 minutes, then 0–70% 400 mM $KH_2PO_4$ (pH 6.3)/60% formamide in 35 minutes.

FIG. 7 is the ion exchange HPLC profile of a phosphodiester linked 20-mer and FIG. 8 is the ion exchange HPLC profile of a phosphorothioate linked 20-mer. Both 20-mers were assembled on 15 µM scale using the above described protocol. FIG. 9 is a melting curve of four different phosphate backbones hybridized to a complementary 20-mer phosphodiester. The smooth transition depicted by the melting curve for all four modified oligonucleotides shows cooperative melting indicating that the method of the subject invention results in high quality product. In addition, unmodified oligonucleotides prepared by the phosphoramidite protocol or by the H-phosphonate method of the subject invention evidenced no difference when tested for antiviral activity. Table 3 lists some of the oligonucleotides synthesized using the above mentioned protocol on an 8 to 16 µmole scale. Table 4 lists sequences prepared on a 100 to 120 µmole scale, a 60-mer produced on an 8 µmole scale and a homosequence of oligoribonucleotide.

TABLE 3

Oligonucleotides Synthesized by the Present Method on an 8-16 µmole Scale

PO - Phosphodiester
PS - Phosphorothioate
PM - Phosphormorpholidate
PB - Phospor-n butylamidate
PP - Phosphor-piperidate

| No. | | Sequence | | | | | | | Modification | Binding Site |
|---|---|---|---|---|---|---|---|---|---|---|
| | 15-mer length | | | | | | | | | |
| 1. | (SA-76) | CCC | AAT | TCT | GAA | AAT | | | PO | HIV-RNA, 5351-5365 |
| 2. | (SA-75) | CTA | ACC | AGA | GAG | ACC | | | PO | HIV-RNA, 1-20 |
| 3. | SA-78 | CCC | AAT | TCT | GAA | AAT | | | PM | HIV-RNA, 5351-5365 |
| 4. | SA-79 | CTA | ACC | AGA | GAG | ACC | | | PM | HIV-RNA, 1-20 |
| 5. | SA-82 | CCC | AAT | TCT | GAA | AAT | | | PS | HIV-RNA, 5351-5365 |
| 6. | SA-80 | CTA | ACC | AGA | GAG | ACC | | | PS | HIV-RNA, 1-20 |
| 7. | SA-96 | CGT | ACT | CAC | CAG | TCG | | | PM | HIV-RNA, 284-298 |
| 8. | SA-97 | CGT | ACT | CAC | CAG | TCG | | | PB | HIV-RNA, 284-299 |
| | 20-mer length | | | | | | | | | |
| 9. | SA-73 | ACA | CCC | AAT | TCT | GAA | AAT | GG | PS | HIV-RNA, 5349-5368 |
| 10. | SA-86 | CGA | GAT | AAT | GTT | CAC | ACA | AC | PS | random sequence |
| 11. | SA-107 | ACA | CCC | AAT | TCT | GAA | AAT | GG | PM | HIV-RNA, 5349-5368 |
| 12. | SA-108 | ACA | CCC | AAT | TCT | GAA | AAT | GG | PP | HIV-RNA, 5349-5368 |
| 13. | SA-109 | GCG | TAC | TCA | CCA | GTC | GCC | GC | PM | HIV-RNA, 280-299 |
| 14. | SA-110 | GCG | TAC | TCA | CCA | GTC | GCC | GC | PP | HIV-RNA, 280-299 |

TABLE 3-continued
Oligonucleotides Synthesized by the Present Method on an 8-16 μmole Scale PO - Phosphodiester
PS - Phosphorothioate
PM - Phosphormorpholidate
PB - Phospor-n butylamidate
PP - Phosphor-piperidate

| No. | | Sequence | | | | | | | Modification | Binding Site |
|---|---|---|---|---|---|---|---|---|---|---|
| 15. | SA-111 | GCG | TAC | TCA | CCA | GTC | GCC | GC | PS | HIV-RNA, 280-299 |
| 16. | SA-112 | ACA | CCC | AAT | TCT | GAA | AAT | GG | PB | HIV-RNA, 5349-5368 |
| 17. | SA-125 | GCA | GGC | AAA | CCA | TTT | GAA | TG | PM | random sequence |
| 18. | SA-128 | CGT | AAG | CAA | CAG | TAG | ATC | CT | PM | random sequence |
| 19. | SA-118 | ACA | CCC | AAT | TCT | GAA | AAT | GG | PO | HIV-RNA, 5349-5368 |
| 20. | SA-120 | CGA | GGC | AAA | CCA | TTT | GAA | TG | PO | Flu vRNA, 8-28 |
| 21. | SA-121 | GCA | GGC | AAA | CCA | TTT | GAA | TG | PS | Flu vRNA, 8-28 |
| 22. | SA-122 | GCA | GGC | AAA | CCA | TTT | GAA | TG | PM | Flu vRNA, 8-28 |
| 23. | SA-123 | GCA | GGC | AAA | CCA | TTT | GAA | TG | PO | Flu vRNA, 8-28 |
| 24. | SA-124 | GCA | GGC | AAA | CCA | TTT | GAA | TG | PS | Flu vRNA, 8-28 |
| 25. | SA-125 | GCA | GGC | AAA | CCA | TTT | GAA | TG | PM | Flu vRNA, 8-28 |
| 26. | SA-499 | CAT | TCA | AAT | GGT | TTG | CCT | GC | PS | complementary to Flu mRNA |
| 27. | SA-527 | CAT | TCA | AAT | GGT | TTG | CCT | GC | PS | complementary to Flu mRNA |
| 28. | SA-528 | GCA | GGC | AAA | CCA | TTT | GAA | TG | PS | Flu vRNA |
| 29. | SA-529 | CGT | AAG | CAA | CAG | TAG | TCC | TA | PS | random |
| 30. | SA-530 | CAC | CCA | ATT | CTG | AAA | ATG | GA | PS | random |
| 31. | SA-531 | CAT | TCA | AAT | GGT | TTG | CCT | GC | PO | Flu mRNA |
| 32. | SA-532 | CAT | TCA | AAT | GGT | TTG | CCT | GC | PS | Flu mRNA |
| 33. | SA-518 | AT | CTT | CAT | CAT | CTG | AGA | GAA | PO | N-myc + c-myc, 1668-1688 |
| 34. | SA-520 | TTC | TTC | CAG | ATG | TCC | TCC | CC | PO | N-myc, 931-950 |
| 35. | SA-525 | AT | CTT | CAT | CAT | CTG | AGA | GAA | PS | N-myc + c-myc 1668-1688 |
| 36. | SA-526 | TTC | TTC | CAG | ATG | TCC | TCC | CC | PS | N-myc, 931-950 |
| 37. | SA-537 | TGA | GGC | TTA | TGC | AGT | GGG | TT | PS | HIV-RNA, 54-73 |
| 38. | SA-539 | GGC | AAG | CTT | TAT | TGA | GGC | TT | PS | HIV-RNA, Poly A |
| 39. | SA-541 | CTG | GTA | GAG | ATT | TTC | CAC | AC | | HIV-RNA, 162-181 |
| 40. | SA-543 | CTG | GTC | TAA | CCA | GAG | AGA | CC | | HIV-RNA, 1-20 |
| | Homosequences | | | | | | | | | |
| 41. | SA-545 | CAA | GTC | CCT | GTT | CGG | GCG | CC | | HIV-RNA, 182-201 |
| 42. | SA-547 | CTC | GCA | CCC | ATC | TCT | CTC | CT | | HIV-RNA, packaging |
| 43. | SA-549 | CTC | CTG | TGT | ATC | TAA | TAG | AG | | HIV-RNA, protease site |
| 44. | SA-73 | CCC | CCC | CCC | CCC | CCC | CCC | CC | PS | |
| 45. | SA-83 | GGG | GGG | GGG | GGG | GGG | GGG | GG | PS | |
| 46. | SA-84 | AAA | AAA | AAA | AAA | AAA | AAA | AA | PS | |
| 47. | SA-85 | TTT | TTT | TTT | TTT | TTT | TTT | TT | PS | |
| 48. | SA-88 | AAA | AAA | AAA | AAA | AAA | AAA | AA | PO | |
| 49. | SA-89 | CCC | CCC | CCC | CCC | CCC | CCC | CC | PO | |
| 50. | SA-90 | GGG | GGG | GGG | GGG | GGG | GGG | GG | PO | |
| 51. | SA-91 | TTT | TTT | TTT | TTT | TTT | TTT | TT | PO | |
| 52. | SA-92 | AAA | AAA | AAA | AAA | AAA | AAA | AA | PM | |
| 53. | SA-93 | CCC | CCC | CCC | CCC | CCC | CCC | CC | PM | |
| 54. | SA-94 | GGG | GGG | GGG | GGG | GGG | GGG | GG | PM | |
| 55. | SA-95 | TTT | TTT | TTT | TTT | TTT | TTT | TT | PM | |

TABLE 4
Oligonucleotides Synthesized by the Present Method on a 100-120 μmole Scale
15 μmole of support was loaded in each column

| No. | | Sequence | | | | | | | | | | | Modification | Binding Site |
|---|---|---|---|---|---|---|---|---|---|---|---|---|---|---|
| 56. | SA-115 | ACA | CCC | AAT | TCT | GAA | AAT GG | | | | | | PO | HIV-RNA, 5349-5368 |
| 57. | SA-116 | ACA | CCC | AAT | TCT | GAA | AAT GG | | | | | | PS | HIV-RNA, 5349-5368 |
| 58. | SA-123 | ACA | CCC | AAT | TCT | GAA | AAT GG | | | | | | PM | HIV-RNA, 5349-5368 |
| 59. | SA-PO | ACA | CCC | AAT | TCT | GAA | AAT GG | | | | | | PO | HIV-RNA, 5349-5368 |
| 60. | SA-PS | ACA | CCC | AAT | TCT | GAA | AAT GG | | | | | | PS | HIV-RNA, 5349-5368 |
| 61. | SA-PM | ACA | CCC | AAT | TCT | GAA | AAT GG | | | | | | PM | HIV-RNA, 5349-5368 |
| | Homosequences were prepared on a 100-120 μmole scale | | | | | | | | | | | | | |
| 62. | SA-T-9 | TTT | TTT | TTT | TTT | TTT | | | | | | | PO | |
| 63. | SA-T-10 | TTT | TTT | TTT | TTT | TTT | | | | | | | PS | |
| 64. | SA-T-11 | CCC | CCC | CCC | CCC | CCC | | | | | | | PO | |
| 65. | SA-T-20 | CCC | CCC | CCC | CCC | CCC | | | | | | | PS | |
| | 60-mer on 8 μmole scale | | | | | | | | | | | | | |
| 66. | SA-60F | ATA | GGT | AAC | GTG | AGG | GCT ACA | CGA | CTG GGG | ACG | CTA AAG | GGG | | |
| | | TTT | ACA | CCC | TTT | GAG | CT | | | | | | | |
| | Homosequences of oligoribonucleotide | | | | | | | | | | | | | |
| 67. | SA-1-R | CCC | CCC | CCC | CCC | CCC | CCC CC | | | | | | | |

Utility

The present invention is for an improved method of synthesizing oligonucleotides. The method makes it possible to carry out efficient monomer coupling with consumption of only 2-3 equivalents of monomers per coupling reaction. For example, a 60 μM scale synthesis (using a 4 columns) can be carried out using the method of the invention in under 8 hours to obtain 200 milligrams of 20-mer, while consuming only 2 grams of monomer. The method is useful in decreasing the cost of conducting a variety of molecular biological techniques in which synthetic oligonucleotides are employed as components.

In "gene screening," synthetic oligonucleotides having a nucleotide sequence complementary to a gene or mRNA of interest are labeled with a reporter group and used to detect the presence of that gene or mRNA in a cDNA or a genomic DNA library.

Synthetic oligonucleotides are also frequently employed as primers for reverse tanscriptase in procedures for synthesizing DNA from a single stranded RNA template. In addition, synthetic oligonucleotides can be used to create specific mutations in a cDNA segment, which can then be reintroduced into the organism to observe the changes in the organism caused by the mutation. This technique is a noteworthy advance over the classical approach of creating in vivo mutations randomly throughout the genome and then isolating those that display a particular phenotype.

Finally, synthetic oligonucleotides (modified or unmodified) are useful as therapeutic or diagnostic agents. For example, they can be used as antiviral agents. An antisense oligonucleotide which is complementary to a portion of a viral mRNA molecule can be synthesized, using known techniques. The antisense oligonucleotide is then introduced to the virus so that it hybridizes with the complementary region of the mRNA in the virus to form a double stranded region. This double stranded region of the viral mRNA cannot be translated. A large amount of synthetic oligonucleotide is required for this purpose (e.g., grams). Thus, the method of the subject invention, which can result in production of large quantities of oligonucleotides, is particularly valuable for this application.

In addition, the method of synthesizing DNA, disclosed herein, has flexibility. Intermediate H-phosphonate can be oxidized to different phosphate backbone modifications. Modified synthetic oligonucleotides have a variety of applications. Phosphorothioate DNA analogs that bear a sulfur in the internucleoside linkage are currently being used as nuclease-resistant anti-sense oligonucleotides either for blocking translation or inhibiting viral DNA synthesis. Marcus-Sekura, C. J. et al. *Nucl. Acid Res* 15:5749-5763 (1987); Agrawal, S. et al., *Proc. Natl Acid. Sci, USA*, 85:7079-7083 (1988). In the past, phosphorothioates have been used to study the stereochemistry of restriction endonucleases (Matsukura, M. et al. *Proc. Nat. Acad. Sci. USA* 84:(1987); Stec, W. J. et al., *J. Amer. Chem. Soc.* 106: Connolly, B. A. et al., *Biochem* 23: 3443-3453 (1984)), the structural dynamics of DNA (Koziolkiewicz, M et al., *Phosphorus and Sulfur* 27: 81-92 (1986)), recognition of DNA by proteins (e.g., monoclonal, anti-native DNA antibodies, LaPlanche, C. A. et al., *Nucl. Acid. Res.* 14: 9081-9093 (1986)), and to elucidate certain enzyme mechanisms, including protein-nucleic acid interactions (Porter, B. and F. Eckstein, *J. Biol. Chem.* 259: 14243 (1984).

Methyl phosphonate analogues of DNA have increased hydrophobicity and have been shown to pass readily through cell membranes and inhibit protein synthesis, presumably by interfering with mRNA translation. Blake, K., et al., *Biochem* 24: 6139 (1985); Smith, C. et al., *Proc. Natl. Acad. Sci USA* 83: 2787 (1986); Agrawal, S. et al., *Tet. Lett.*, 28: 3539-3542 (1987); Sarin, P. S. et al., *Proc. Natl. Acad. Sci. USA*, 85: 7448-7451 (1988).

Phosphoramidate analogues of oligonucleotides are known to bind to complementary polynucleotides and have been used for the attachment of various ligands to DNA. Letsinger, R. et al., *Nucl. Acids Res.* 14: 3487 (1986); Agrawal, S. et al., *Proc. Natl. Acad. Sci. USA*, 85: 7079-7083 (1988).

All of the aforementioned basic and applied molecular biological techniques employing synthetic oligonucleotides will benefit from the method of the subject invention, whereby oligonucleotides can be synthesized on a large scale, with high coupling efficiency and consuming only 2-3 equivalents of H-phosphonate nucleotide monomers per coupling reaction.

Equivalents

Those skilled in the art will recognize or be able to ascertain using no more than routine experimentation, many equivalents to the specific embodiments of the invention described herein. These and all other equivalents are intended to be encompassed by the following claims.

We claim:

1. An improved process for synthesizing oligonucleotides by condensing a solid support-bound nucleotide with free activated nucleoside H-phosphonate monomer, wherein the improvement comprises producing the activated nucleoside H-phosphonate monomer by combining nucleoside H-phosphonate monomer and an activator in a ratio of less than one part monomer to five parts activator, and allowing the activated nucleoside H-phosphonate to react with the solid support-bound nucleotide for about 15 seconds or less.

2. The improved process according to claim 1, wherein the ratio of H-phosphonate monomer to activator is one part monomer to about ten parts activator.

* * * * *

UNITED STATES PATENT AND TRADEMARK OFFICE
CERTIFICATE OF CORRECTION

PATENT NO. : 5,149,798
DATED : September 22, 1992
INVENTOR(S) : Sudhir Agrawal and Paul C. Zamecnik It is certified that error appears in the above-indentified patent and that said Letters Patent is hereby corrected as shown below:

Column 1, delete lines 7-8 and insert the following therefor:

--This invention was made with government support under grant numbers AI-24846-03 and GM-21595-15 from the National Institutes of Health. The government has certain rights in the invention.--

Signed and Sealed this

Sixteenth Day of August, 1994

Attest:

BRUCE LEHMAN

*Attesting Officer*    *Commissioner of Patents and Trademarks*